(12) United States Patent
Farnham

(10) Patent No.: US 7,632,966 B2
(45) Date of Patent: Dec. 15, 2009

(54) SYNTHESIS OF TRITHIOCARBONATE RAFT AGENTS AND INTERMEDIATES THEREOF

(75) Inventor: William Brown Farnham, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/578,268

(22) PCT Filed: May 11, 2005

(86) PCT No.: PCT/US2005/016584

§ 371 (c)(1),
(2), (4) Date: Oct. 11, 2006

(87) PCT Pub. No.: WO2005/113493

PCT Pub. Date: Dec. 1, 2005

(65) Prior Publication Data

US 2008/0039651 A1    Feb. 14, 2008

(51) Int. Cl.
*C07C 327/00*  (2006.01)
*C07C 329/00*  (2006.01)
*C01B 31/00*   (2006.01)

(52) U.S. Cl. .................. 562/28; 423/414; 558/243; 558/244; 528/196

(58) Field of Classification Search ............ 526/31, 526/79, 82, 85, 86; 528/196; 558/243, 244; 562/28; 423/414
See application file for complete search history.

(56) References Cited

U.S. PATENT DOCUMENTS

| | | | |
|---|---|---|---|
| 2,574,829 A * | 11/1951 | Himel et al. | 558/245 |
| 2,600,737 A * | 6/1952 | Crouch et al. | 558/243 |
| 2,676,974 A * | 4/1954 | Crouch et al. | 558/244 |
| 2,893,835 A * | 7/1959 | Stone et al. | 423/414 |
| 4,197,311 A * | 4/1980 | Wepplo et al. | 514/471 |

OTHER PUBLICATIONS

Gareau et al. Free Radical Reaction of Diisopropyl Xanthogen Disulfide with Unsaturated Systems, 1998, Heterocycles, vol. 48, No. 10, 2008, 2016.*
Thang, et al. A Novel Systhesis of Functional Dithioesters, Dithiocarbamates, Xanthates and Trithiocarbonates, Tetrahedron Letters, 1999, vol. 40, No. 13, 2436, 2437.*

* cited by examiner

Primary Examiner—Porfirio Nazario-Gonzalez
Assistant Examiner—Yate' K Cutliff
(74) Attorney, Agent, or Firm—Konrad S. Kaeding

(57) ABSTRACT

This invention provides an efficient method for synthesizing trithiocarbonate RAFT agents, RSC(S)SR', that can be used in the living polymerization of methacrylates and other olefinic monomers. This invention also provides an efficient method of synthesizing bis(alkylsulfanylthiocarbonyl) disulfides that are useful as intermediates in the synthesis of trithiocarbonate RAFT agents.

10 Claims, No Drawings

SYNTHESIS OF TRITHIOCARBONATE RAFT AGENTS AND INTERMEDIATES THEREOF

FIELD OF THE INVENTION

This invention provides an efficient method for synthesizing trithiocarbonate RAFT agents, RSC(S)SR', that can be used in the living polymerization of methacrylates and other olefinic monomers. This invention also provides an efficient method for synthesizing bis(alkylsulfanylthiocarbonyl) disulfides that are useful as intermediates in the synthesis of trithiocarbonate RAFT agents.

BACKGROUND

RAFT (reversible addition fragmentation chain transfer) polymerization processes have been disclosed for the preparation of low-polydispersity polymers from acrylic, styrenic and selected other vinyl monomers. (WO 98/01478, WO 99/31144 and EP 0 910,587).

Trithiocarbonates have been identified as suitable RAFT agents for polymerizing methacrylates, but commercially attractive methods for their preparation have been lacking. For example, methods that convert a thiol to the corresponding sodium salt typically involve the use of NaH, a hazardous material to handle at large scale. Other methods (e.g., electron transfer alkylation) have been used for trithiocarbonate synthesis, but are unattractive due to low yields and the difficult purification procedures required.

A continuing needs exists for an efficient and scalable process for RAFT agents.

SUMMARY OF THE INVENTION

This invention provides a process comprising reacting a thiol, RSH, sequentially with sodium or potassium t-butoxide, carbon disulfide and iodine in a solvent mixture comprising 80-99 vol % of a first solvent and 1-20 vol % of second solvent to form RSC(S)SSS(S)SR, wherein:

R=a substituted or unsubstituted $C_1$-$C_{20}$ linear or $C_3$-$C_6$ cyclic alkyl, a substituted or unsubstituted aryl, or a heterocyclic group;

the first solvent is selected from a group consisting of n-alkanes and cyclic alkanes; and the second solvent is selected from a group consisting of ethers with a solvent polarity parameter $E_T(30)$, of at least 36 kcalmol$^{-1}$.

DETAILED DESCRIPTION

The process of this invention provides a practical route for the synthesis of bis(alkylsulfanylthiocarbonyl) disulfides, (RSC(S)SSC(S)SR) and the preparation of a wide variety of useful RAFT agents. The bis(alkylsulfanylthiocarbonyl) disulfides are useful intermediates in the synthesis of the RAFT agents.

In one embodiment of this invention, a thiol, RSH, is reacted sequentially with sodium or potassium t-butoxide, carbon disulfide and iodine in a solvent mixture comprising 80-99 vol % of a first solvent and 1-20 vol % of second solvent to form RSC(S)SSC(S)SR.

Suitable alkyl thiols, RSH, are those in which R is a substituted or unsubstituted $C_1$-$C_{20}$ linear or $C_3$-$C_6$ cyclic alkyl group, a substituted or unsubstituted aryl group, or a heterocyclic group. Suitable substitutents include halo, cyano, aryl, alkoxy, carboalkoxy and acetoxy groups. In a preferred embodiment, R is $C_{12}H_{25}$.

Suitable first solvents include $C_5$-$C_{10}$ n-alkanes and cyclic alkanes. Suitable second solvents include linear ethers such as 1,2-dimethoxyethane, 2-methoxyethyl ether, diethylene glycol dimethyl ether, diethylene glycol diethyl ether, and cyclic ethers such as tetrahydrofuran (THF) and 1,4-dioxane. In a preferred embodiment, the first solvent is heptane and the second solvent is THF.

Applicant has found that the use of hydrocarbons such as n-alkanes (e.g., heptane) as principal solvent, with a small volume (1-20%) of a second characterized by a solvent polarity parameter, $E_T(30)$, of at least 36 kcalmol$^{-1}$, facilitates the formation of the desired product. In one embodiment, a small volume fraction (5-20%) of tetrahydrofuran allows for >99% conversion of dodecane thiol to bis(dodecylsulfanylthiocarbonyl) disulfide in >98+% selectivity. In this way, a simple isolation of the bis(dodecylsulfanylthiocarbonyl) disulfide intermediate is sufficient for use of this bis(alkylsulfanylthiocarbonyl) disulfide in the synthesis of RAFT agents.

The definition of "solvent polarity parameter" and a list of these parameters for common solvents can be found in "Solvents and Solvent Effects in Organic Chemistry", Christian Reichardt, 1$^{st}$ reprint of the 2$^{nd}$ ed., VCH, 1990, pp. 359-371.

In another embodiment, this invention further comprises reacting the bis(alkylsulfanylthiocarbonyl) disulfide, RSC(S)SSC(S)SR, with R'—N=N—R' to form RSC(S)SR'.

Suitable R' groups include substituted or unsubstituted $C_1$-$C_{10}$ linear or $C_3$-$C_6$ cyclic alkyl groups. Suitable substitutents include halo, cyano, aryl, alkoxy, carboxy, carboalkoxy and acetoxy groups.

One embodiment of the process of this invention is shown in the Scheme to illustrate the synthesis of RAFT agents. However, the process is not limited to this particular example, and can be used for a wide variety of thiols and diazo compounds.

Scheme

1) $2\ C_{12}H_{25}SH + 2\ ^tBuOK + 2\ CS_2 + I_2 \longrightarrow$ $C_{12}H_{25}SC(S)SSC(S)SC_{12}H_{25}$

2) $C_{12}H_{25}SC(S)SSC(S)SC_{12}H_{25} +$ 4,4'-azobis(4-cyanopentanoic acid) $\longrightarrow$ $2\ C_{12}H_{25}SC(S)SC(CH_3)(CN)CH_2CH_2CO_2H$ Step (2) of the Scheme can be carried out using staged addition of the diazo reagent to an ethyl acetate solution of the bis(alkylsulfanylthiocarbonyl) disulfide at modest temperature.

In some cases, it is desirable to convert the acid group of RAFT agents such as $C_{12}H_{25}SC(S)SC(CH_3)(CN)CH_2CH_2CO_2H$ to an ester. This can be accomplished by reacting the acid form of the RAFT agent with an alkyl iodide (e.g., methyl iodide) in the presence of a base (e.g., DBU=1,8-diazabicyclo[5.4.0]undec-7-ene):

$C_{12}H_{25}SC(S)SC(CH_3)(CN)CH_2CH_2CO_2H+DBU+$
$CH_3I \rightarrow C_{12}H_{25}SC(S)SC(CH_3)(CN)$
$CH_2CH_2CO_2CH_3$ This avoids solid/liquid interface problems, and produces easily recovered DBU/HI by-product. Alternatively, methyl and alkoxymethyl esters can be produced in essentially quantitative fashion using dimethyl sulfate or chloromethyl alkyl ethers, chloromethyl cycloalkyl ethers and chloromethyl polycyclic alkyl ethers as alkylating agents and potassium carbonate as base. Alkylating agents are generally compounds with functionalized alkyl fragments that are susceptible to nucleolphilic attack.

EXAMPLES

Example 1

Preparation of Bis(Dodecylsulfanylthiocarbonyl) Disulfide

A 2000 mL 4-neck round bottom flask (fitted with mechanical stirrer, septum, thermocouple well, and reflux condenser with $N_2$ bubbler) was charged with heptane (1000 mL) and a solution of potassium t-butoxide in tetrahydrofuran (174.4 g, containing 34.7 g potassium t-butoxide, 0.31 mol). The resulting solution was cooled to ca. 5° C. and reacted with dodecanethiol (60.6 g, 0.30 mol, Sigma-Aldrich Co., Milwaukee, Wis.). The resulting white slurry was stirred for 30 min at 5-10° C. and then reacted with carbon disulfide (23.5 g, 0.31 mol) over a 20 min period. The mixture was stirred at 5° C. for 10 min, allowed to warm to 20-23° C. and stirred for 4 h. The resulting yellow slurry was reacted in portions with iodine (40.0 g, 0.158 mol) over a 40 min period at 16-18° C. The mixture was stirred at room temperature for 15 h. Distilled water was added, and the separated organic phase was washed with a solution of sodium chloride and sodium thiosulfate, then with sodium chloride solution. The organic layer was dried and the solvent was evaporated to provide 84.2 g (98%) of yellow solid. $^1$H NMR (CDCl$_3$): 3.28 (t, J=7.4, a=97.75), 2.92 (minor triplet a=2.1), 2.66 (very minor triplet, a=0.52), 1.68 (apparent quintet, a=102.0), 1.43 to 1.17 (remaining CH$_2$ signals, a=914), 0.87 (t, J=7.0, a=153.1).

Example 2

Preparation of 4-Cyano-4-(dodecylsulfanythiocarbonyl)sulfanyl Pentanoic Acid

A 2 liter, 3-neck flask fitted with reflux condenser, solids addition port, thermowell, and stir bar was charged with bis (dodecylsulfanylthiocarbonyl) disulfide (84.1 g, 151.6 mmol) and 760 mL ethyl acetate. The resulting solution was heated to gentle reflux and reacted with 4,4'-azobis(4-cyanopentanoic acid) (72.1 g, 257 mmol) (Wako Chemicals USA, Inc., Richmond, Va.) over 3.75 h. The reaction mixture was heated for an additional 16 h.

Ethyl acetate was removed under reduced pressure and the product was allowed to crystallize from heptane. The solid was filtered, washed with water, and dried to provide 110.0 g (91%). $^1$H NMR (CDCl$_3$): 3.31 (t, a=2.00), 2.72 to 2.61 (m) and 2.58 to 2.34 (AB pattern with additional coupling, combined a=3.96), 1.87 (s, a=2.94), 1.68 (m, a=2.02), 1.42 to 1.20 (overlapping CH$_2$ signals, a=18.62), 0.87 (t, a=3.07), bd acid peak at ca. 10.0. Purity>99%. $^{13}$C NMR (CDCl$_3$): 216.91 (C=S), 177.52 (CO$_2$H), 118.96 (CN), 46.38, 37.24, 33.65, 32.01, 29.72 (overlapping signals), 29.68, 29.64, 29.52, 29.43, 29.17, 29.03, 27.79, 24.97, 22.78, 20.12, 14.20.

Example 3

Preparation of Methyl 4-Cyano-4-(dodecylsulfanythiocarbonyl)sulfanyl Pentanoate

A solution of 4-cyano-4-(dodecylsulfanythiocarbonyl)sulfanyl pentanoic acid (C$_{12}$H$_{25}$SC(S)SC(Me)(CN) CH$_2$CH$_2$CO$_2$H, 64.8 g, 160.5 mmol) in THF (195 mL) at 5-10° C. was treated with diazabicyclo[5.4.0]undec-7-ene (26.9 g, 176.6 mmol). The mixture was stirred for 5 min, then treated with methyl iodide (25.9 g, 182 mmol), and the resulting mixture was stirred for 18 hr.

The reaction mixture was diluted with heptane, filtered, and the solid was rinsed with heptane. The filtrate was washed successively with dilute sodium chloride, 1N hydrochloric acid, dilute sodium bicarbonate solution, and water. The dried organic phase was evaporated to give 64.13 g (96%) of amber oil.

$^1$H NMR: (CDCl$_3$): 3.70 (s, a=3.00), 3.31 (t, a=2.04), 2.66 to 2.56 (m, a=2.05) and 2.54 to 2.33 (AB pattern with additional coupling, a=2.05), 1.86 (s, a=3.02), 1.68 (m, a=2.27), 1.42 to 1.20 (overlapping CH$_2$ groups, a=19.24), 0.87 (t, a=3.28).

Example 4

Preparation of Methoxymethyl Ester

A mixture of 4-cyano-4-(dodecylsulfanythiocarbonyl)sulfanyl pentanoic acid (1.21 g, 3.0 mmol), THF (10 mL), and freshly ground potassium carbonate (0.42 g, 3 mmol) was treated with chloromethyl methyl ether (0.25 mL, 3.1 mmol, Sigma-Aldrich Co., Milwaukee, Wis.). The mixture was heated at 40° C. and stirred for 18 h. The mixture was filtered and solid was washed with ethyl acetate. Evaporation provided 1.31 g viscous oil. $^1$H NMR (CDCl$_3$): 5.24 (s, a=2.01), 3.47 (s, a=3.01), 3.31 (t, a=2.00), 2.70 to 2.61 (m, a=2.15), 2.56 to 2.34 (AB pattern with additional couplings, a=2.07), 1.87 (s, a=2.85), 1.68 (m, a=2.17), 1.38 (m) and 1.32 to 1.2 (overlapping CH$_2$'s, a=21.1), 0.87 (t, a=3.50). Consistent with desired ester; purity estimate=95%.

Comparative Example A

Attempted Synthesis of Bis(dodecylsulfanylthiocarbonyl) Disulfide

A 1000 mL 4-neck round bottom flask (fitted with mechanical stirrer, septum, thermocouple well, and condenser with $N_2$ inlet) was charged with a solution of potassium t-butoxide (17.2 g, 0.153 mol) in tetrahydrofuran (200 mL). The solution was cooled to ca. 5° C. and treated with dodecanethiol (30.3 g, 0.15 mol). The reaction mixture was stirred for 30 min at 5-10° C. The thick slurry was treated with carbon disulfide (11.8 g, 0.154 mol) over a ca. 30 min period. The mixture became yellow. The mixture was stirred at ca. 0° C. for 1 h and then was allowed to warm to room temperature. The resulting yellow solution was treated in portions with iodine prills (19.0 g, 0.075 mol) over a 20 min period, keeping the temperature controlled below 28-30° C. When iodine addition was complete, the mixture was stirred for 1.5 h. Ethyl acetate (300 mL) was added, and the mixture was treated with water (50 mL) and then with sodium thiosulfate solution (50 mL) and stirred vigorously. The organic layer was washed twice with sodium chloride solution, dried over $Na_2SO_4$, and evaporated to give only 31.6 g of almost colorless solid. $^1H$ NMR featured a major downfield $CH_2S$ signal at 2.67, and only traces of other triplet signals in the 3.4 to 2.8 range. The mass spectrum exhibited parent ion with m/e=402.335, consistent with $C_{24}H_{50}S_2$, bis(dodecyl) disulfide.

What is claimed is:

1. A process comprising:

reacting a thiol, RSH, sequentially with sodium or potassium t-butoxide, carbon disulfide and iodine in a solvent mixture comprising 80-99 vol % of a first solvent and 120 vol % of second solvent to form RSC(S)SSC(S)SR; wherein R= a substituted or unsubstituted $C_1$-$C_{20}$ linear or $C_3$-$C_6$ cyclic alkyl, a substituted or unsubstituted aryl, or a heterocyclic group;

the first solvent is selected from a group consisting of $C_5$-$C_{10}$ n-alkanes and cyclic alkanes; and the second solvent is selected from a group consisting of ethers with a solvent polarity parameter, $E_t(30)$, of at least 36 kcalmol$^{-1}$.

2. The process of claim 1, wherein R is $C_{12}H_{25}$.

3. The process of claim 1, further comprising reacting RSC(S)SSC(S)SR with R'—N=N—R' to form RSC(S)SR', wherein R' is selected from a group consisting of substituted or unsubstituted $C_1$-$C_{10}$ linear alkyl groups and $C_3$-$C_6$ cyclic alkyl groups.

4. The process of claim 3, wherein R' is substituted with substitutents selected from a group consisting of halo, cyano, aryl, alkoxy, carboxy, carboalkoxy and acetoxy groups.

5. The process of claim 3, wherein R' is —C(CH$_3$)(CN)CH$_2$CH$_2$CO$_2$H.

6. The process of claim 3, wherein R' is —C(CH$_3$)(CN)CH$_2$CH$_2$CO$_2$H and the process further comprises reacting RSC(S)SR' with an alkylating agent.

7. The process of claim 6, wherein the alkylating agent is selected from a group consisting of alkyl iodides, dimethyl sulfate, chloromethyl alkyl ethers, chloromethyl cycloalkyl ethers and chloromethyl polycyclic alkyl ethers.

8. The process of claim 1, wherein the second solvent is selected from a group consisting of linear ethers and cyclic ethers with a solvent polarity parameter, $E_t(30)$, of at least 36 kcalmol$^{-1}$.

9. The process of claim 8, wherein the linear ether is selected from a group consisting of 1,2-dimethoxyethane, 2-methoxyethyl ether, diethylene glycol dimethyl ether, and diethylene glycol diethyl ether.

10. The process of claim 8, wherein the cyclic ether is selected from a group consisting of tetrahydrofuran (THF) and 1,4-dioxane.

* * * * *

UNITED STATES PATENT AND TRADEMARK OFFICE
CERTIFICATE OF CORRECTION

PATENT NO. : 7,632,966 B2
APPLICATION NO. : 11/578268
DATED : December 15, 2009
INVENTOR(S) : Farnham William Brown It is certified that error appears in the above-identified patent and that said Letters Patent is hereby corrected as shown below:

Column 5, Line 15, please change "120 vol%" to read -- 1-20 vol% --.

Column 5, Line 24, please change "kcalmol $^{1}$." to read -- kcalmol$^{-1}$. --.

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

PATENT NO.        : 7,632,966 B2                    Page 1 of 1
APPLICATION NO.   : 11/578268
DATED             : December 15, 2009
INVENTOR(S)       : William Brown Farnham It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 164 days.

Signed and Sealed this

Second Day of November, 2010

David J. Kappos
*Director of the United States Patent and Trademark Office*